(12) United States Patent
Behymer et al.

(10) Patent No.: US 9,943,294 B2
(45) Date of Patent: Apr. 17, 2018

(54) ANCHOR DEPLOYMENT FOR IMPLANTABLE MEDICAL DEVICES

(71) Applicant: Medtronic, Inc., Minneapolis, MN (US)

(72) Inventors: Bruce A. Behymer, Grant, MN (US); Michael J. Kern, St. Louis Park, MN (US); William V. Ferris, Jr., Minneapolis, MN (US); Thomas C. Bischoff, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/400,140

(22) Filed: Jan. 6, 2017

(65) Prior Publication Data

US 2017/0112479 A1    Apr. 27, 2017

Related U.S. Application Data

(62) Division of application No. 14/179,766, filed on Feb. 13, 2014, now Pat. No. 9,566,049.

(60) Provisional application No. 61/776,200, filed on Mar. 11, 2013.

(51) Int. Cl.
| | |
|---|---|
| *A61M 25/02* | (2006.01) |
| *A61B 17/00* | (2006.01) |
| *A61N 1/05* | (2006.01) |

(52) U.S. Cl.
CPC ............ *A61B 17/00* (2013.01); *A61M 25/02* (2013.01); *A61N 1/057* (2013.01); *A61N 1/0558* (2013.01); *A61M 2025/028* (2013.01); *A61M 2025/0286* (2013.01); *Y10T 29/49895* (2015.01)

(58) Field of Classification Search
CPC .................. A61B 17/00; A61M 25/02; A61M 2025/0286; A61M 2025/028; A61N 1/0558; A61N 1/057; Y10T 29/49895
See application file for complete search history.

(56) References Cited

U.S. PATENT DOCUMENTS

| | | |
|---|---|---|
| 2008/0275401 A1 | 11/2008 | Sage |
| 2009/0198197 A1 | 8/2009 | Bischoff |
| 2011/0040257 A1 | 2/2011 | Behymer et al. |

(Continued)

OTHER PUBLICATIONS

PCT/US2014/016239—International Search Report and Written Opinoin, dated Apr. 8, 2014.

*Primary Examiner* — Sarang Afzali
*Assistant Examiner* — Ruth G Hidalgo-Hernandez
(74) *Attorney, Agent, or Firm* — Rick L. Franzen

(57) ABSTRACT

A tool for deploying an anchor sleeve onto an implantable device includes handle and base members, which may be fitted together by an operator. The operator may select the handle member from a plurality thereof included in a kit; and the base member, also included in the kit, includes a rail segment with which a gripping portion of the selected handle member may be engaged, for example, via guidance from a marked portion of the base member. Once engaged, a deployment tip of the base member is located to move a mounted anchor sleeve from a tubular member of the handle member and onto a body of the device. The tubular member of some tools has a laterally offset distal end portion, on which the corresponding anchor sleeve is mounted; thus, kits including this type of handle member, may include a converter for the base member to facilitate engagement therewith.

7 Claims, 12 Drawing Sheets

(56) References Cited

U.S. PATENT DOCUMENTS

2012/0232624 A1 9/2012 Sage
2013/0012989 A1 1/2013 Sage et al.

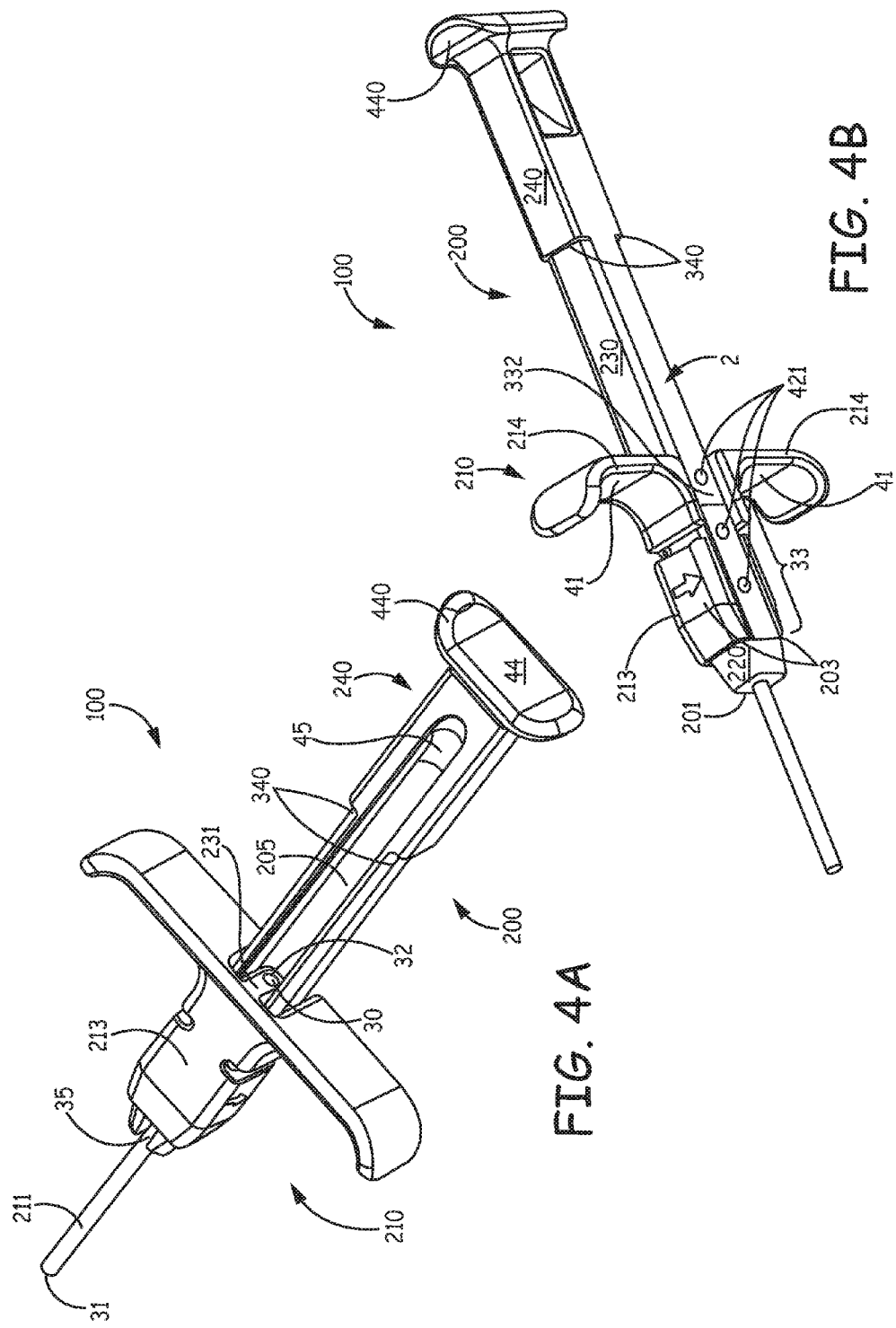

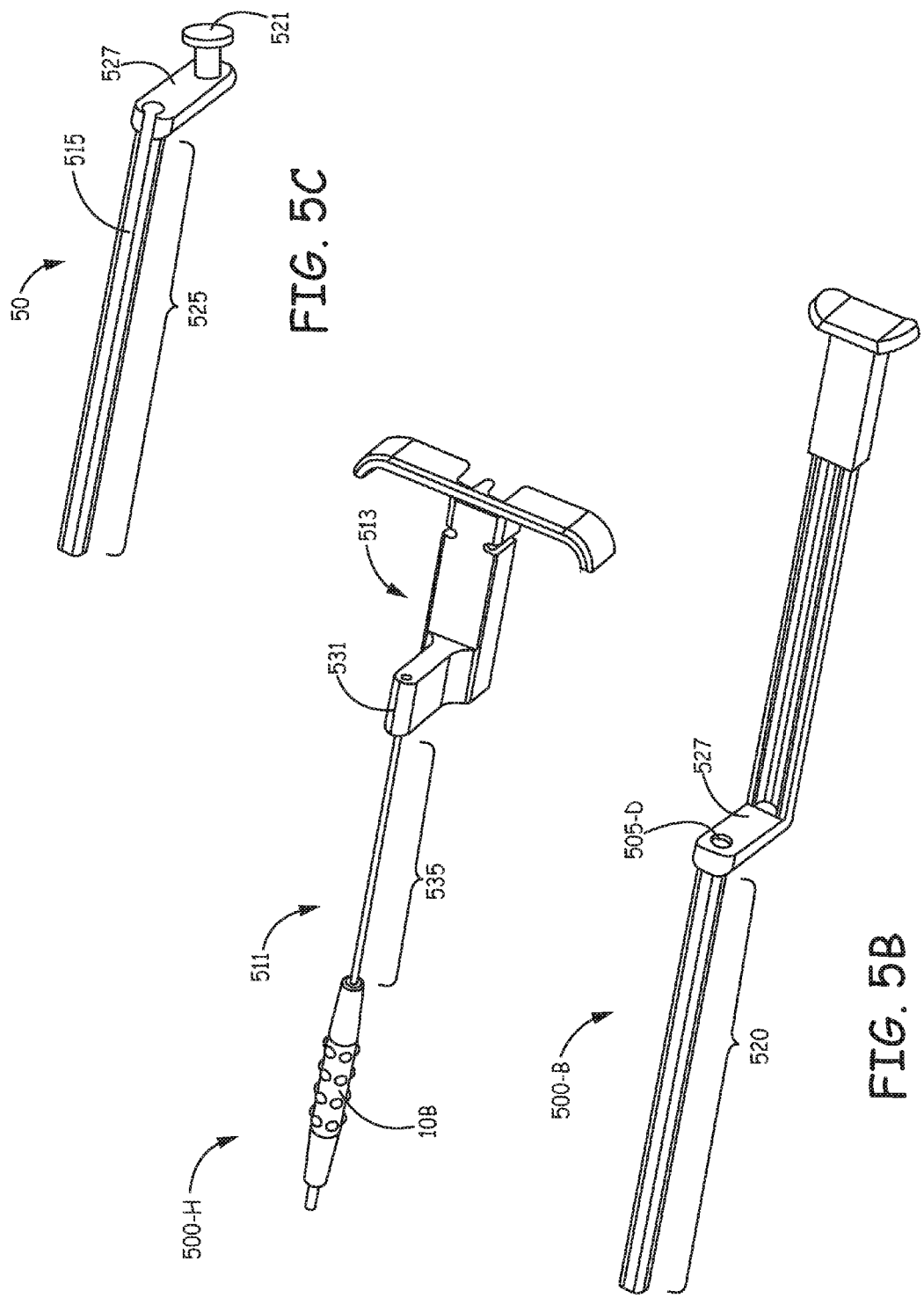

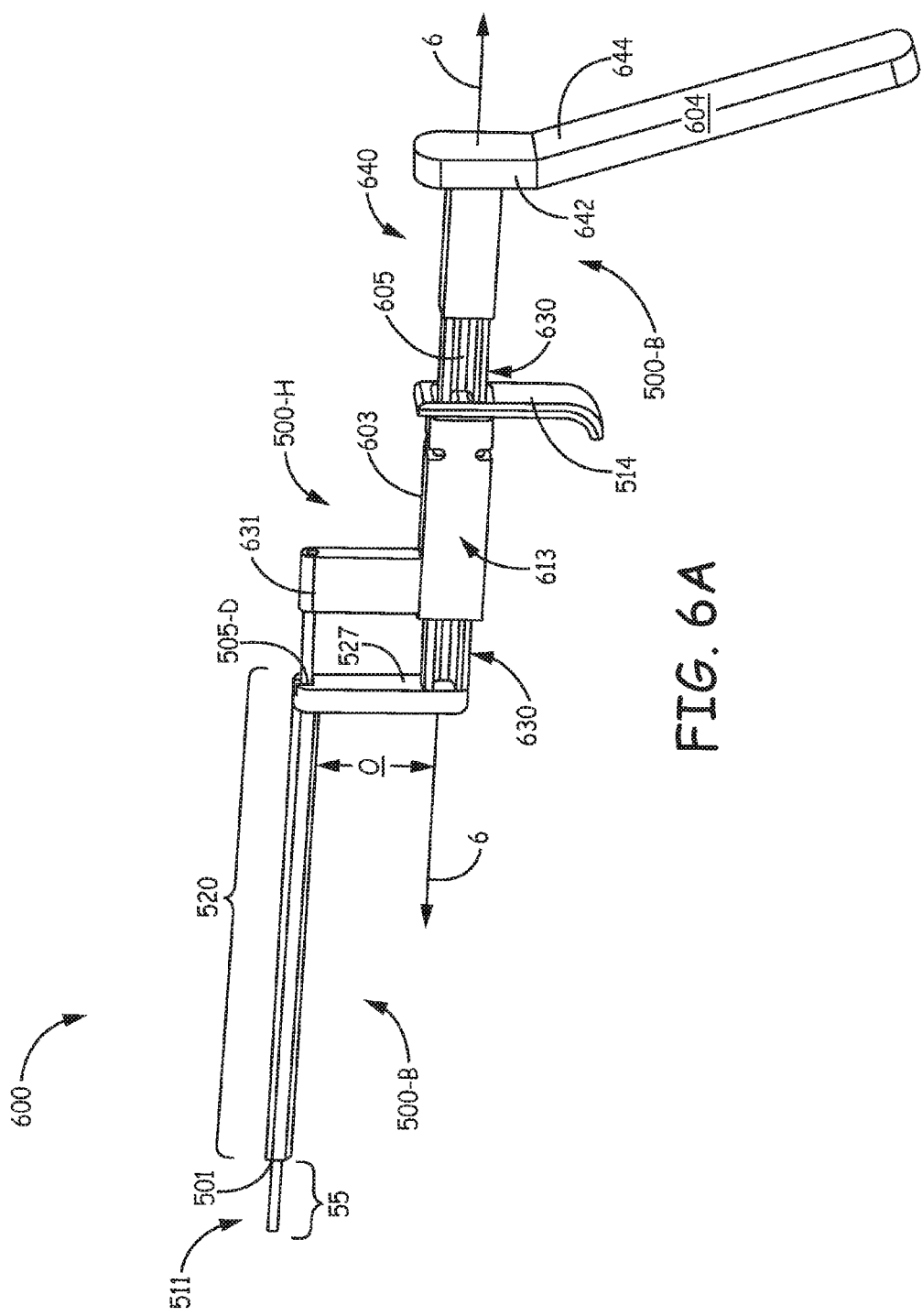

ANCHOR DEPLOYMENT FOR IMPLANTABLE MEDICAL DEVICES

This application is a divisional application of U.S. application Ser. No. 14/179,766, filed Feb. 13, 2014, now allowed, which claims the benefit of U.S. Application No. 61/776,200. The entire content of each of these U.S. Applications is incorporated herein by reference.

TECHNICAL FIELD

The present disclosure is related to implantable medical devices, and more particularly to anchor deployment apparatus and methods.

BACKGROUND

A variety of elongate implantable medical devices, for example, drug delivery catheters and medical electrical leads, are known in the art, for example, to couple a therapy delivery generator and/or diagnostic devices to a target site within a body of a patient, for example, in the spinal column or in any of a number of internal organs. Those skilled in the art are familiar with apparatus and methods for anchoring these implanted devices. FIG. 1A is a schematic depicting a surgical incision site 12 through which an exemplary elongate medical device 110 has been implanted. FIG. 1A illustrates a length of device 110 extending proximally out from site 12 and an anchor sleeve 10 surrounding a body of device 110, for example, with a relatively tight, interference fit, to facilitate anchoring of device 110 to subcutaneous fascia 14, for example, via sutures tied thereabout and sewn into the fascia 14. Anchor sleeve 10 may be any of a variety of types known in the art such as types 10A, 10B and 10C shown in FIG. 1B. In order to properly position such a snug fitting anchor sleeve 10 around the body of implanted device 110, an anchor deployment tool may be employed. Examples of such a tool are described in a co-pending and commonly assigned United States Patent Application having the pre-grant publication no. 2011/0040257, and the Ser. No. 12/896,147.

BRIEF DESCRIPTION OF THE DRAWINGS

The following drawings are illustrative of particular embodiments of the present disclosure and therefore do not limit the scope. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 4A-B are perspective views of the exemplary deployment tool, according to some embodiments;

FIG. 5B is an exploded perspective view of the exemplary tool of FIG. 5A;

FIG. 5C is a perspective view of an exemplary converter for a kit, according to some embodiments;

FIG. 6A is a perspective view of an exemplary deployment tool, according to some additional embodiments;

DETAILED DESCRIPTION

The following detailed description is exemplary in nature and is not intended to limit the scope, applicability, or configuration of the disclosure in any way. Rather, the following description provides practical examples, and, after reading the present disclosure, those skilled in the art will recognize that some of the examples may have suitable alternatives.

Figure 1A:
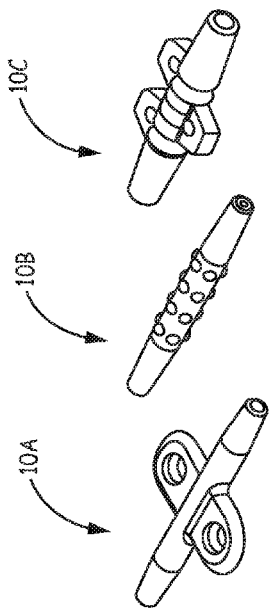
FIG. 1A is a schematic depicting a surgical incision site through which an exemplary elongate medical device has been implanted.
Figure 1B:
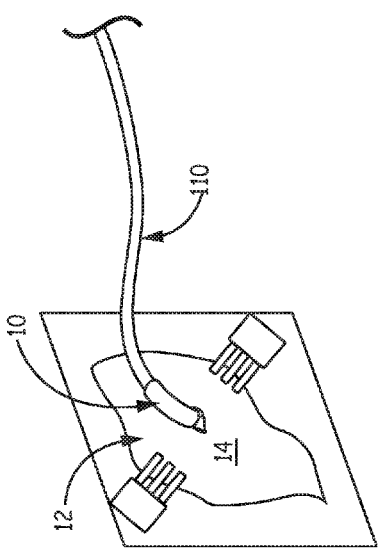
FIG. 1B is a perspective view of a variety of types of exemplary anchor sleeves.
Figure 1C:
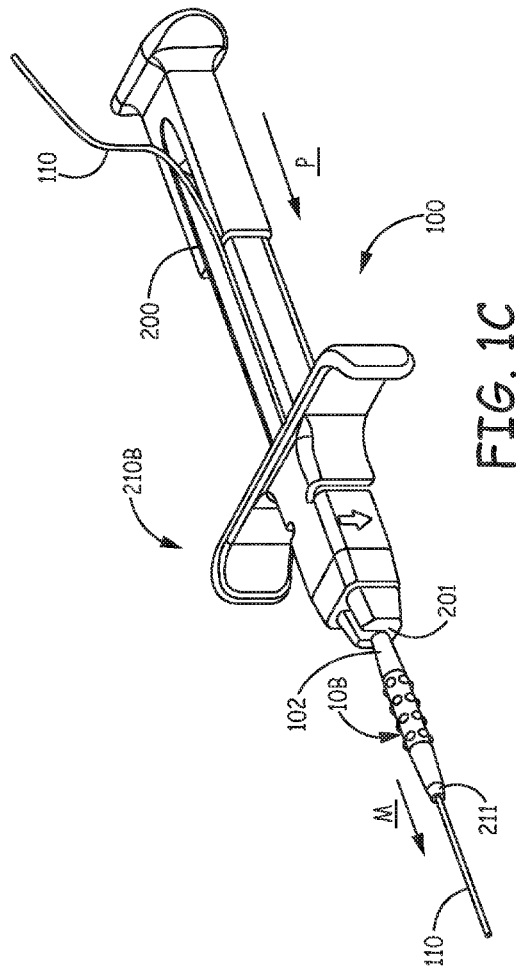
FIG. 1C is a perspective view of an exemplary anchor deployment tool positioned around a proximal length of the exemplary medical device, according to some embodiments.

FIG. 1C is a perspective view of an exemplary anchor deployment tool 100 positioned around a proximal length of medical device 110, according to some embodiments. FIG. 1C illustrates tool 100 including a base member 200 and a handle member 210B, which is held in sliding engagement with base member 200, for example, by a gripping portion 213 thereof; handle member 210B is shown including an elongate tubular member 211 on which anchor sleeve 10B is mounted. A longitudinal axis 15 of tool 100 may be defined by a rail segment 230 of base member 200 and/or by gripping portion 213 of handle member 210B. FIG. 1C further illustrates base member 200 including a deployment tip 201, which is located in close proximity to anchor sleeve 10B. According to the illustrated embodiment, when base member 200 is pushed, per arrow P, relative to handle member 210B and device 110, deployment tip 201 engages a proximal end 102 of anchor sleeve 10B to move sleeve 10B off tubular member 211, per arrow M, and onto medical device 110. With reference to FIG. 4A, which is a different perspective view of tool 100, it may be seen that an inner surface of tubular member 211 defines a lumen 30, which extends from an opening at a distal end 31 of member 211 to an opening at a proximal end 32 of member 211, and which is sized to receive, in sliding engagement, the proximal length of implanted device 110, as shown in FIG. 1C. FIG. 4A further illustrates a channel 205 of base member 200, which also receives the proximal length of device 110, as shown in FIG. 1C.

Figure 2:
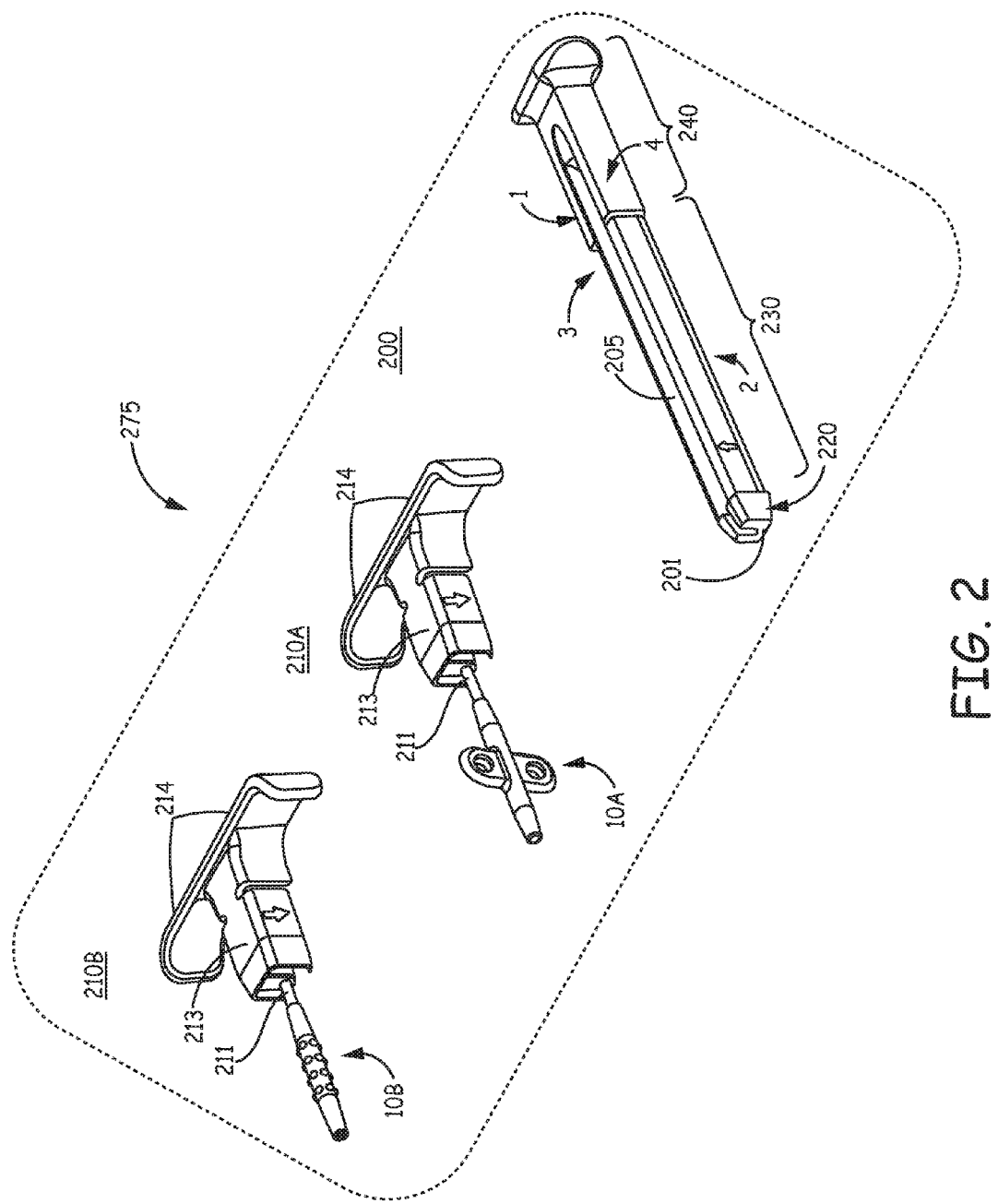
FIG. 2 is a perspective view of members of an exemplary kit, according to some embodiments.

FIG. 2 is a perspective view of members of the exemplary deployment tool 100, which may be included in an exemplary kit 275, according to some embodiments. Kit 275 is shown including base member 200 and, separated therefrom, at least two types of handle member 210, wherein the two types, 210A and 210B, differ from one another only in that handle member 210A has anchor sleeve 10A mounted thereon and handle member 210B has anchor sleeve 10B mounted thereon. FIG. 2 illustrates tubular member 211 of each handle member 210A, 210B extending distally from gripping portion 213 of the corresponding handle member 210A, 210B. FIG. 2 further illustrates base member 200 including a distal segment 220, a proximal segment 240, and rail segment 230, which has recessed opposing sidewalls 3, 4, and which extends between distal segment 220 and shoulders 340 of proximal segment 240; channel 205, which is formed in a first side 1 of base member 200, extends proximally from an opening at deployment tip 201, through distal segment 220, and through rail segment 230, and into proximal segment 240. According to the illustrated embodiment, rail segment 230 and channel 205 of base member 200 are configured to receive gripping portion 213 of either handle member 210A, or handle member 210B in sliding engagement, as will be described in greater detail below. Thus, kit 275 provides an operator a choice of at least two types of pre-mounted anchor sleeves, which choice may be a matter of functional requirements for a particular implant location and/or personal preference, and which saves the operator the trouble of mounting the selected anchor sleeve onto handle member 210. It should be noted that alternate kit embodiments include additional similar handle members on which other types of sleeves are mounted, and/or different types of handle members with pre-mounted anchor sleeves, and/or other elements, which will described below, in conjunction with FIGS. 5A-6C.

Figure 3A:
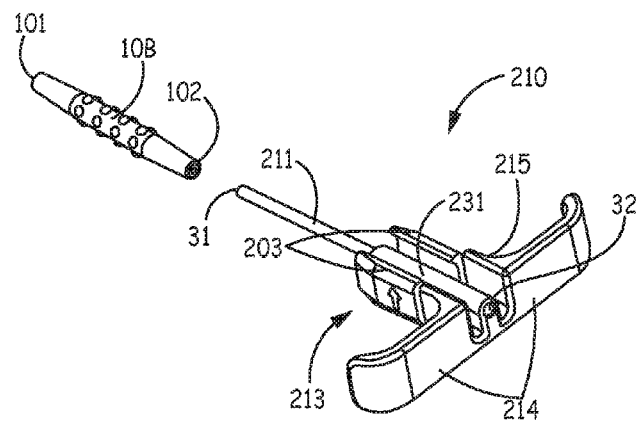
FIG. 3A is a perspective view of an anchor sleeve positioned relative to a handle member of the exemplary deployment tool, for assembly thereon, according to some embodiments.

FIG. 3A is a perspective view of anchor sleeve 10B positioned relative to handle member 210, for assembly thereon. According to some preferred embodiments, so that sleeve 10B effectively grips around device 110, after being deployed thereon, sleeve 10B is formed from an elastic material, for example, medical grade silicone rubber, and has a relaxed inner diameter that is smaller than an outer diameter of device 110. As mentioned above, the inner surface of tubular member 211 defines a lumen which receives a proximal length of device 110, so a diameter of the outer surface of tubular member 211 is such that sleeve 10 is stretched, or expanded, when mounted on tubular member 211. Distal end 31 of tubular member 211 may be formed with a taper, and/or a tapered lead-in tip (not shown) may be temporarily coupled to distal end 31 to facilitate the assembly of sleeve 10B onto member 211. According to some preferred embodiments, tubular member 211 is a stainless steel hypo-tube with a lubricious coating forming the outer surface thereof, for example, a fluoropolymer coating (PTFE or ETFE), which can facilitate the assembly of sleeve 10B onto member 211, as well as the movement of sleeve 10B off of member 211 and onto device 110, by engagement of deployment tip 201 of tool 100, as described above, in conjunction with FIG. 1C.

Figure 3B:
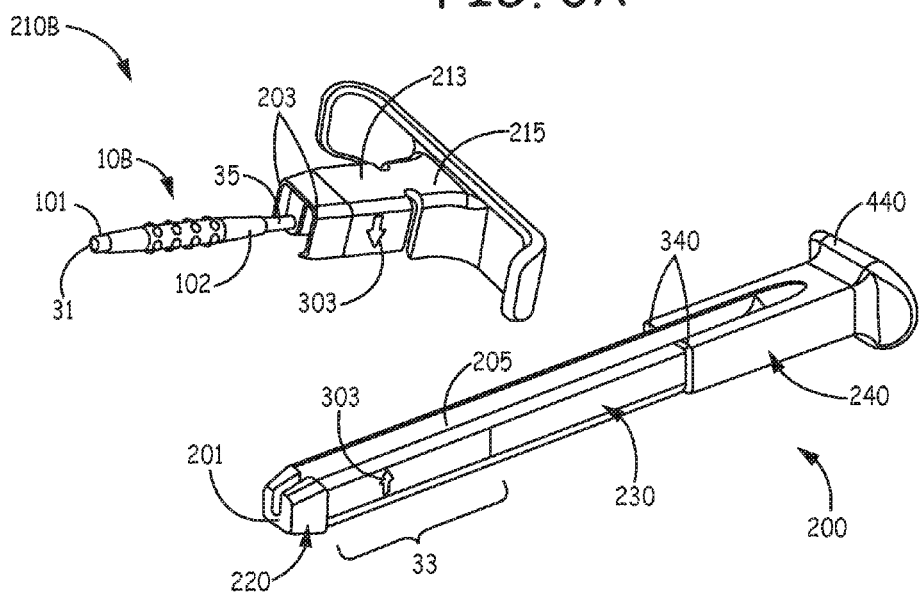
FIG. 3B is a perspective view of the handle member positioned for fitting together with a base member to form the exemplary deployment tool, according to some embodiments and methods.

According to some embodiments of the present disclosure, after sleeve 10B is mounted on tubular member 211, handle member 210B is packaged along with other handle members, such as handle member 210A, and base member 200, to form a kit, such as exemplary kit 275 (FIG. 2), which is ultimately delivered to an operator who is implanting an elongate medical device, such as device 110. Thus, according to some methods of the present disclosure, the operator may select and remove from kit 275 one of handle members 210A, 210B and base member 200 to form a deployment tool, after implanting the device. For example, with reference to FIG. 3B, the operator selects handle member 210B and positions handle member 210B relative to base member 200, as shown, to fit the two members together and, thereby, form tool 100. FIG. 3B shows base member 200 including an optional exemplary alignment mark, for example, a marked portion 33, located in proximity to distal segment 220, and shows base member 200 located with respect to handle member 210B, so that optional marked portion 33 is approximately aligned with gripping portion 213 of handle member 210B. Optional marked portion 33 may be formed by an arrow mark 303 and/or a strip, or length, of colorant that contrasts with a color of the remainder of rail segment 230; arrow mark 303 may facilitate a proper orientation of channel 205 toward handle member 210B. Handle member 210B may also include arrow mark 303 formed on gripping portion 213, as shown, which further facilitates alignment and the proper orientation of handle member 210B for fitting together with base member 200.

After properly aligning and orienting handle member 210B and base member 200, the operator engages marked portion 33 of base member 200 with gripping portion 213 of handle member 210B, for example, by positioning a rearward alignment portion 215 of handle member 210B around rail segment 230, and then pressing gripping portion 213 and marked portion 33 of rail segment 230 together in the direction indicated by arrow marks 303. With further reference to FIGS. 3B and 4A, when handle member 210 is engaged with base member 200, as facilitated by marked portion 33, a segment 35 of tubular member 211 of handle member 210B, which extends between proximal end 102 of mounted anchor sleeve 10B and gripping portion 213, is received in a portion of channel 205 that passes through distal segment 220 of base member 200, such that deployment tip 201 of base member 200 is in close proximity to end 102 of mounted sleeve 10B, as shown in FIG. 1C. According to the illustrated embodiment, gripping portion 213 includes opposing arms 203 that flex outward and then snap into place around rail segment 230, as rail segment 230 is inserted therebetween, so that arms 203 hold handle member 210B in sliding engagement with rail segment 230 of base member 200.

With further reference to FIG. 3A, a junction between tubular member 211 and gripping portion 213 is formed by a press fit of a proximal length of tubular member 211 within a bore hole that is formed through an inner ridge 231 of gripping portion 213, wherein inner ridge 231 extends between opposing arms 203 and is configured to fit in sliding engagement within channel 205 of base member 200, when arms 203 are fitted around rail segment 230. According to some embodiments, the junction between tubular member 211 and gripping portion 213 is further formed by flaring proximal end 32 of tubular member 211, so that the flared end abuts a surface of ridge 231 that extends around an opening of the bore hole. According to some exemplary embodiments, base member 200 and handle member 210 are each formed, for example, by injection molding, from a suitable hard plastic material, for example, polycarbonate; and a stainless steel hypo-tube that forms tubular member 211 may be press fit into inner ridge 231 following molding, or handle member 210 may be insert molded around tubular member 211.

According to some methods, the operator may insert the proximal length of the implanted elongate device, for example, device 110, through lumen 30 of tubular member 211 prior to fitting handle member 210B together with base member 200; alternately, members 210B, 200 may be fitted together and then the proximal length of the implanted device inserted through lumen 30. In either case, once members 210B, 200 are assembled together and the proximal length of device 110 inserted through the lumen of tubular member 211, sleeve 10B may be deployed (e.g., moved off of tubular member 211 of handle member 210), as described above in conjunction with FIG. 1C. With reference to FIG. 1C, in conjunction with FIGS. 4A-B, the operator may push base member 200, with respect to handle member 210, per arrow P, by placing a fingers of his hand against an abutment surface 41 of each laterally extending tab element 214 of handle member 210, and placing a thumb of the hand against another abutment surface 44 of base member 200, which is formed at a proximal terminal end 440 thereof.

With reference to FIG. 4B, according to some embodiments, optional marked portion 33 of rail segment 230, for example, when formed by the aforementioned length of contrasting color, extends along a second side 2 of base member 200, and has a length which is approximately equal to that of anchor sleeve 10B, so that, according to some methods, the operator may monitor the movement of marked portion 33 relative to gripping portion 213 of handle member 210, while pushing base member 200, to determine when sleeve 10B has been completely moved off tubular member 211. For example, when the operator sees that a proximal end 332 of the length of marked portion 33 has moved distal to gripping portion 213, he may use this as an indication that sleeve 10B is deployed around device 110. FIG. 4B further illustrates second side 2 of base member 200 including holes 421 formed therethrough, wherein holes 421 are located along rail segment 230 in proximity to distal segment 220. Thus, if tool 100 is assembled for packaging (rather than being disassembled in kit form), with arms 203 of handle member 210 fitted around base member 200 in the above-described aligned engagement (with proximal end 102 of mounted anchor sleeve 10B located for engagement with deployment tip 201, as shown in FIG. 1C), holes 421 will allow sterilization gases to flow into that portion of channel 205 where ridge 231 of handle member 210 is received.

With further reference to FIGS. 1C and 4A, channel 205 extends into proximal portion 240 of base member 200 and is terminated by a ramped portion 45, for example, to provide a smooth exit transition for the proximal length of device 110 that is received in channel 205 while sleeve 10B is being deployed thereon. FIGS. 3B and 4A-B, further illustrate shoulders 340 of proximal segment 240 of base member 200 being located proximal to ramped portion 45 of channel 205 to stop the sliding engagement of handle member 210 with base member 200, along rail segment 230, so as to prevent inadvertent pinching of device 110 in channel 205, when deploying anchor sleeve 10B via pushing base member 200, per arrow P.

Figure 5A:
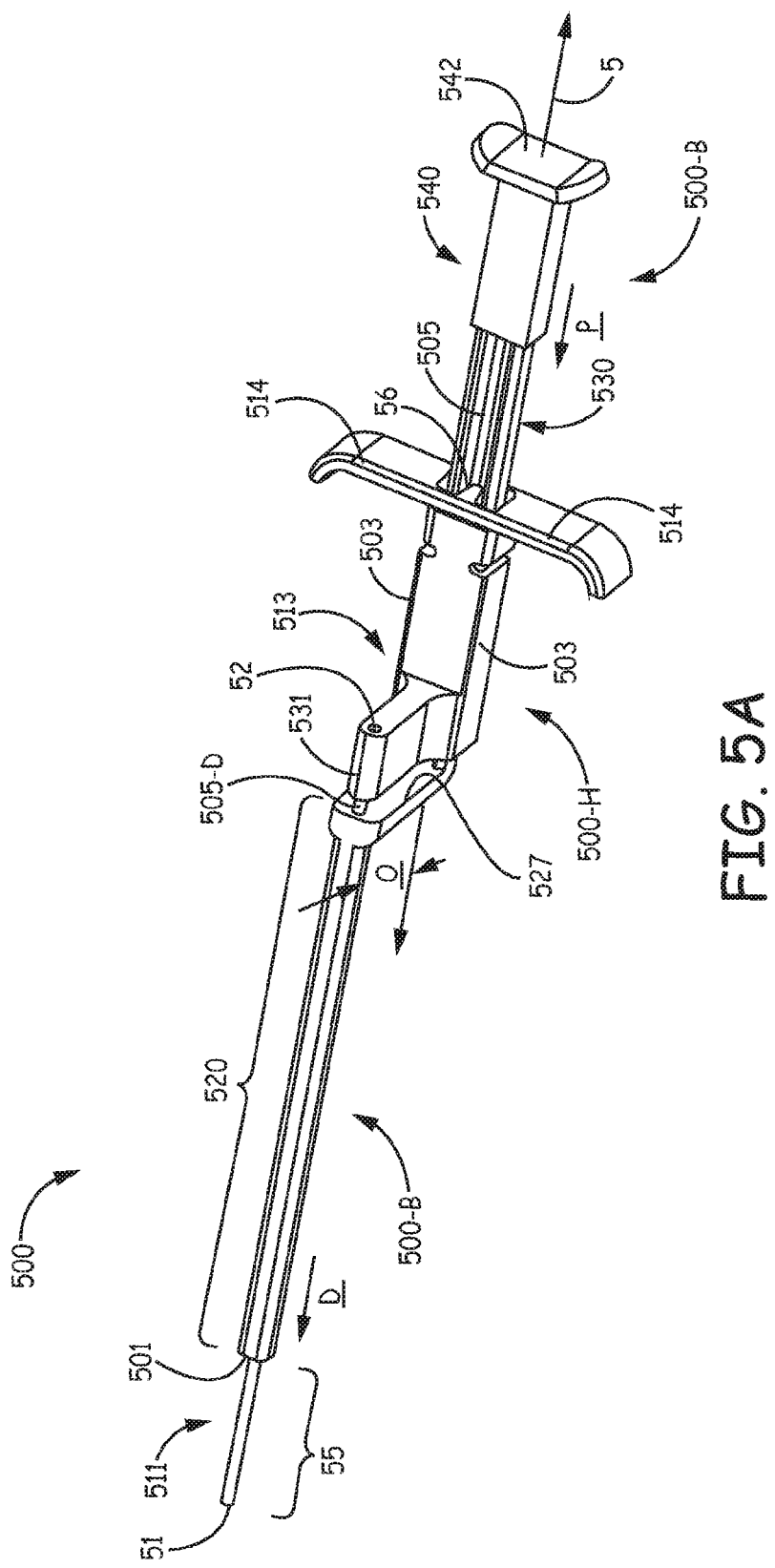
FIG. 5A is a perspective view of an exemplary deployment tool, according to some alternate embodiments.

FIG. 5A is a perspective view of an exemplary deployment tool 500, according to some alternate embodiments; and FIG. 5B is an exploded perspective view of tool 500. FIGS. 5A-B illustrate tool 500 including a base member 500-B and a handle member 500-H, wherein handle member 500-H includes a gripping portion 513 and an elongate tubular member 511, which is laterally offset from gripping portion 513, and which extends distally from a junction in an outward protruding ridge 531 of gripping portion 513; an inner surface of tubular member 511 defines a lumen that extends from an opening at a distal end 51 of member 511 to an opening at a proximal end 52 of member 511 to accommodate insertion of a proximal length of an implanted elongate device, such as device 110 (FIG. 1A). FIG. 5B further illustrates base member 500-B including a distal segment 520, through which a channel 505-D extends to receive tubular member 511 of handle portion 500-H in sliding engagement therewith, and a rail segment 530, about which opposing arms 503 of gripping portion 513 of handle member 500-H are fitted for sliding engagement therewith. With further reference to FIGS. 5A-B, rail segment 530 of base member 500-B, or gripping segment 513 of handle member 500-H, may define a longitudinal axis 5 of tool 500, and distal segment 520 is shown including a leg member 527 that offsets segment 520 from axis 5 by a distance O, so that the laterally offset tubular member 511 of handle member 500-H may be received within channel 505-D, when gripping portion 513 is fitted together with rail segment 530. Although FIGS. 5A-B illustrate rail segment 530 including a channel 505-R, which receives an inward protruding ridge 56 of gripping segment 513 of handle member 500-H, for example, to stabilize the engagement between base member 500-B and handle member 500-H, ridge 56 and channel 505-R might be excluded from alternate embodiments.

According to the illustrated embodiment, a distal end portion 55 of tubular member 511 extends distally, from a deployment tip 501 of base member 500-B, and over a length sufficient to accommodate mounting of an anchor sleeve around an outer surface thereof, for example, sleeve 10B shown in FIG. 5B. The lateral offset of distal end portion 55 from gripping portion 513 of handle member 500-H provides clearance between an insertion site of an implanted device, for example, device 110, and those portions of tool 500 that are engaged by an operator between fingers and thumb, namely laterally extending tab elements 514 of handle member 500-H, and proximal terminal end 542 of base member 500-B, to push base member 500-B, per arrows P and D, relative to handle member 500-H, and, thereby, deploy the mounted anchor sleeve. Moreover, a length of distal segment 520 may be approximately four inches or more, to accommodate an anchor site that is located deeper within the fascia than that illustrated in FIG. 1A, or to accommodate an anchor site that is located below the fascia.

According to some embodiments, handle member 500-H, separate from base member 500-B, may be included in a kit, such as exemplary kit 275 (FIG. 2), with an anchoring sleeve mounted thereon, as shown in FIG. 5B, wherein the kit further includes a converter, for example, a converter 50, which is shown in FIG. 5C. FIG. 5C illustrates the exemplary converter 50 including a pin member 521, which extends from leg member 527, for coupling converter 50 to base member 200 (FIG. 2), for example, via a press fit within the portion of channel 205 that extends along distal segment 220, so that base member 200 may converted into a configuration, that is similar to base-member 500-B of FIG. 5B, to accommodate laterally offset tubular member 511 of handle member 500-H, when engaged therewith. FIG. 5C further illustrates converter 50 including an auxiliary open channel 515 formed in an auxiliary distal segment 525 to receive a segment 535 of tubular member 511 (FIG. 5B) during the fitting together of handle member 500-H and the converted base member 200, for example, generally according to steps described above in conjunction with FIG. 3B. Although not shown, handle member 500-H may further include the above-described arrow mark 303 on one on both of opposing arms 503 of gripping portion 513, similar to handle members 210A, 210B, to facilitate alignment and proper orientation of handle member 500-H for fitting together with base member 200, in a manner similar to that described above, in conjunction with FIG. 3B.

Figure 6B:
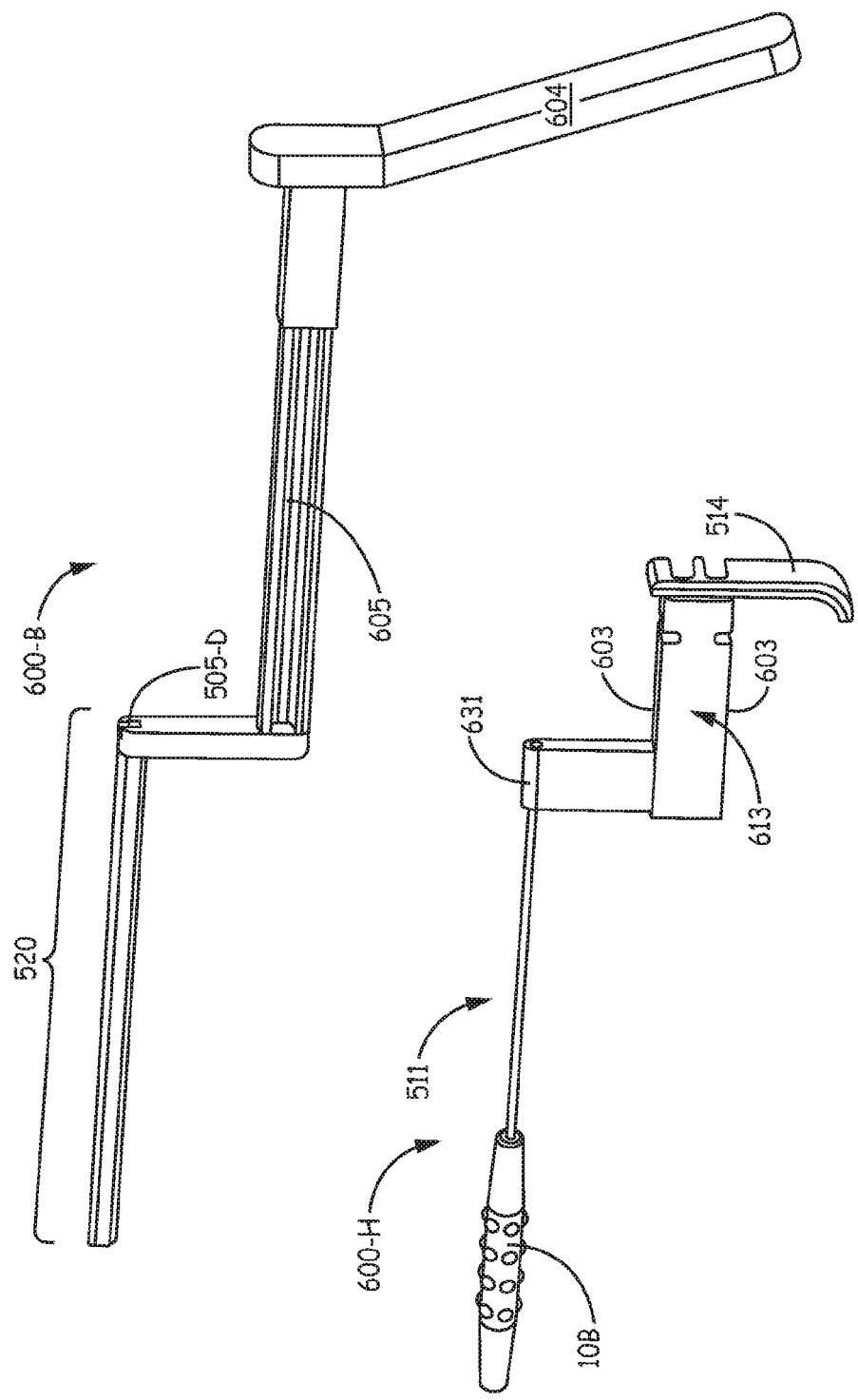
FIG. 6B is an exploded perspective view of the exemplary tool of FIG. 6A.

FIG. 6A is a perspective view of an exemplary deployment tool 600, according to some additional embodiments; and FIG. 6B is an exploded perspective view of tool 600. Tool 600, like tool 500 (FIGS. 5A-B), provides the above-described clearance for the operator during anchor sleeve deployment, since a handle member 600-H thereof includes tubular member 511 laterally offset from a gripping portion 613 thereof, and a base member 600-B thereof includes distal segment 520, with channel 505-D extending therethrough, which is offset, by distance O, from a longitudinal axis 6 of tool 600 by a leg member 627, to accommodate the offset of tubular member 511. Tool 600 differs from tool 500 in that a proximal end 642 of base member 600-B has a heel element 644 extending therefrom, and only one of laterally extending tab elements 514 is included in handle member 600-H, for use in conjunction with heel element 644, wherein the operator may engage the single tab element 514 with one or more fingers while abutting a heel of his hand against a proximal surface 604 of heel element 644 to push base member 600-B relative to handle member 600-H for the deployment of mounted anchor sleeve 10B (shown in FIG. 6B) from distal end portion 55 of tubular member 511. With further reference to FIGS. 6A-B, tool 600 also differs from tool 500 in that an outward protruding ridge 631 of gripping portion 613, which forms the junction with tubular member 511, and leg member 627 of base member 600-B extend in generally the same plane as laterally extending tab element 514; and opposing arms 603 of gripping portion 613, which extend around rail segment 630 of base member 600-B to hold handle member 600-H in sliding engagement with rail segment 630 of base member 600-B, extend in a direction approximately orthogonal to the extent of ridge 613.

Figure 6C:
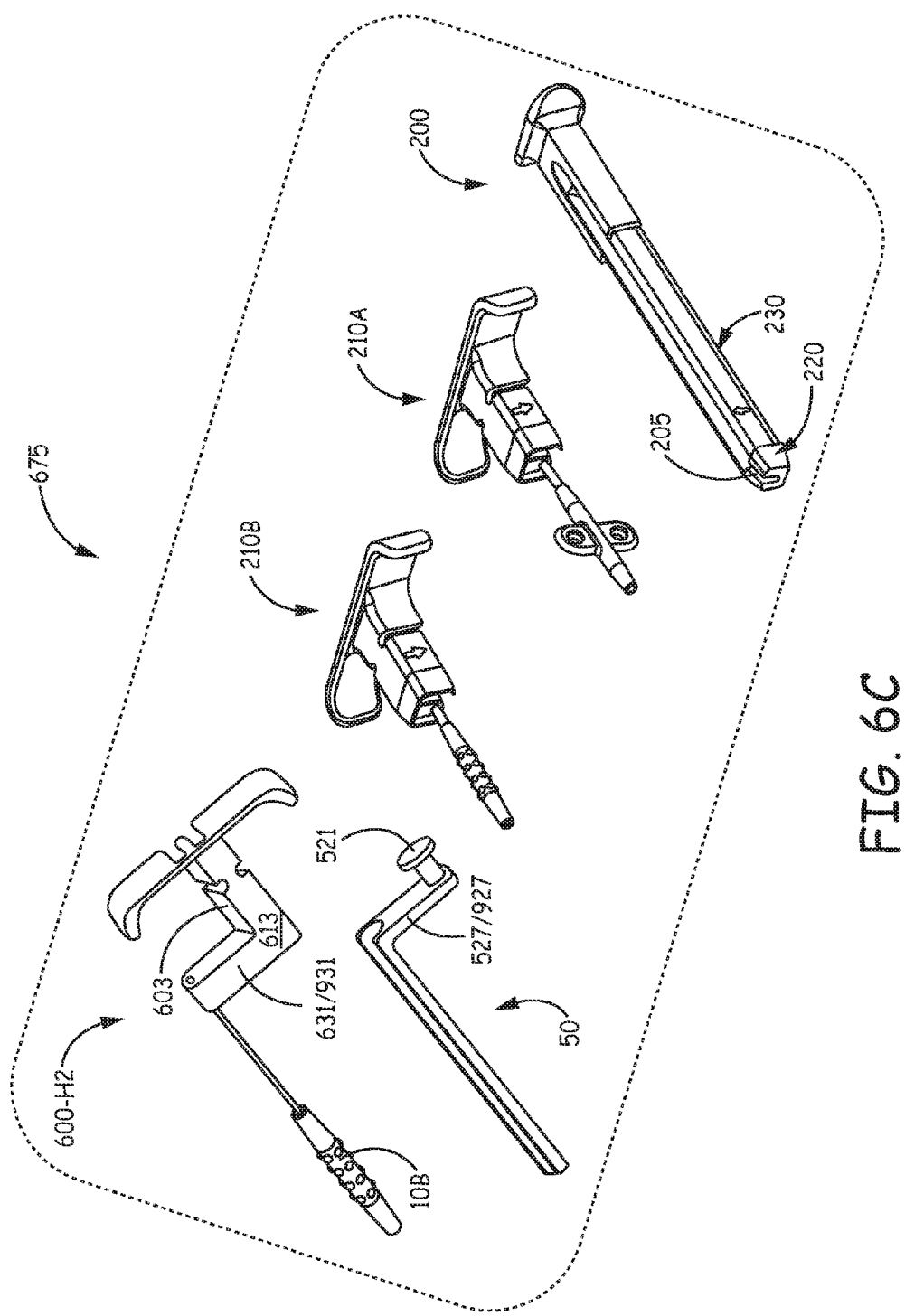
FIG. 6C is a perspective view of members of an exemplary kit, according to some alternate embodiments.

FIG. 6C is a perspective view of members of an exemplary kit 675, according to some alternate embodiments. FIG. 6C illustrates the members of kit 675 including handle members 210A, 210B, base member 200, converter 50, and a handle member 600-H2 with mounted anchor sleeve 10B, which is similar to handle-member 600-H, but includes two laterally extending tab elements 514. According to the illustrated embodiment, converter 50 may be coupled to base member 200, via the press fit of pin member 521 within channel 205 along distal segment 220, to form a converted base member, which is similar to base member 600-B of FIG. 6B, but without heel element 644. Although not shown, handle member 600-H2 may include the above-described arrow mark 303 on one on both of opposing arms 603 of gripping portion 613, similar to handle members 210A, 210B, to facilitate alignment and proper orientation of handle member 600-H2 for fitting together with base member 200, in a manner similar to that described above, in conjunction with FIG. 3B. Like opposing arms 203 of handle members 210A, 210B, arms 603 flex outward and then snap into place around rail segment 230 of base member 200, as rail segment 230 is inserted therebetween.

Figures 6D, 6E:
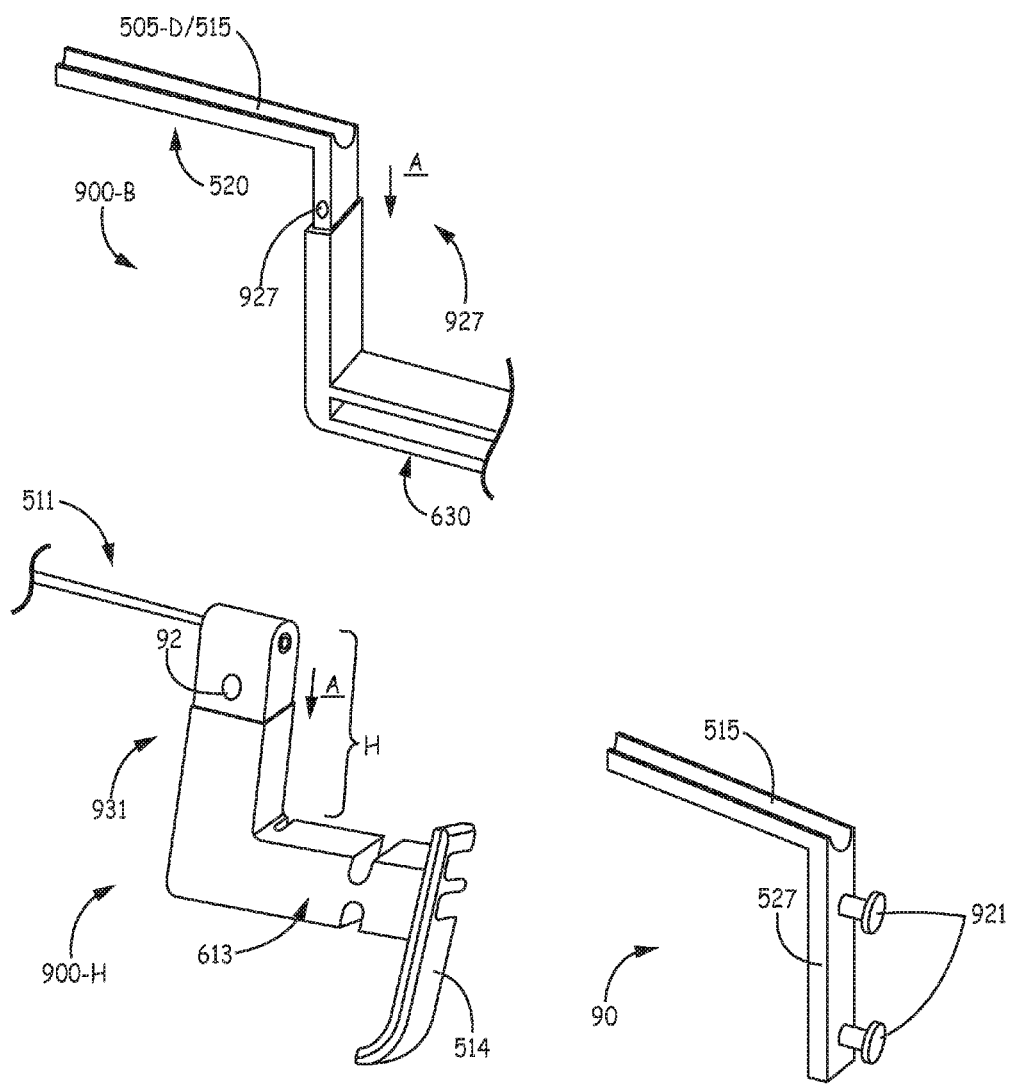
FIG. 6D is an exploded perspective view of portions of an exemplary adjustable tool, according to some alternate embodiments.
FIG. 6E is a perspective view of an exemplary converter, according to some alternate embodiments.

FIG. 6D is an exploded perspective view of portions of an exemplary adjustable tool, according to some alternate embodiments. FIG. 6D illustrates a portion of an adjustable base member 900-B alongside a portion of an adjustable handle member 900-H, which, when fitted together with base member 900-B, forms a tool similar to tool 600, described in conjunction with FIGS. 6A-B. Handle member 900-H, like handle member 600-H, includes gripping portion 613 and tab element 514, but a height H of an outward protruding ridge 931 of handle member 900-H, which joins tubular member 511 to gripping portion 613, is adjustable to vary a lateral offset of tubular member 511 from gripping portion 613. Likewise, a leg member 927 of base member 900-B is adjustable to vary distance O of the lateral offset of distal segment 520 (FIG. 6A) from rail segment 630 so that the offset corresponds to the adjusted height H of ridge 931 to accommodate tubular member 511 in a channel 915 (may be open, as shown, or closed like channel 505-D) of distal segment 520, when handle member 900-H and base member 900-B are fitted together in sliding engagement. According to FIG. 6D, ridge 931 and leg member 927 are each adjustable, for example, per arrows A, by means of a telescoping configuration, and each may include detent features 92 to secure ridge 931 to leg member 927 at at least two different offsets.

With reference back to FIG. 6C, handle member 600-H2 may be configured to include adjustable outward protruding ridge 931, wherein, according to an alternate embodiment of kit 675, converter 50 may be configured with adjustable leg member 927. Alternately, kit 675 may include a plurality of converters having leg members 527 of different lengths, to correspond to the various adjustments of handle member 600-H2 that is configured with adjustable ridge 931. Or, for example, with reference to FIG. 6E, another type of adjustable converter 90 may be included in kit 675, in lieu of converter 50. FIG. 6E illustrates the exemplary converter 90 including a pair of pin members 921 extending from leg member 527, wherein one of pin members 921 is selected to couple converter 90 to base member 200 according to selected offset (e.g. height H) of the adjustable handle member.

Figure 7:
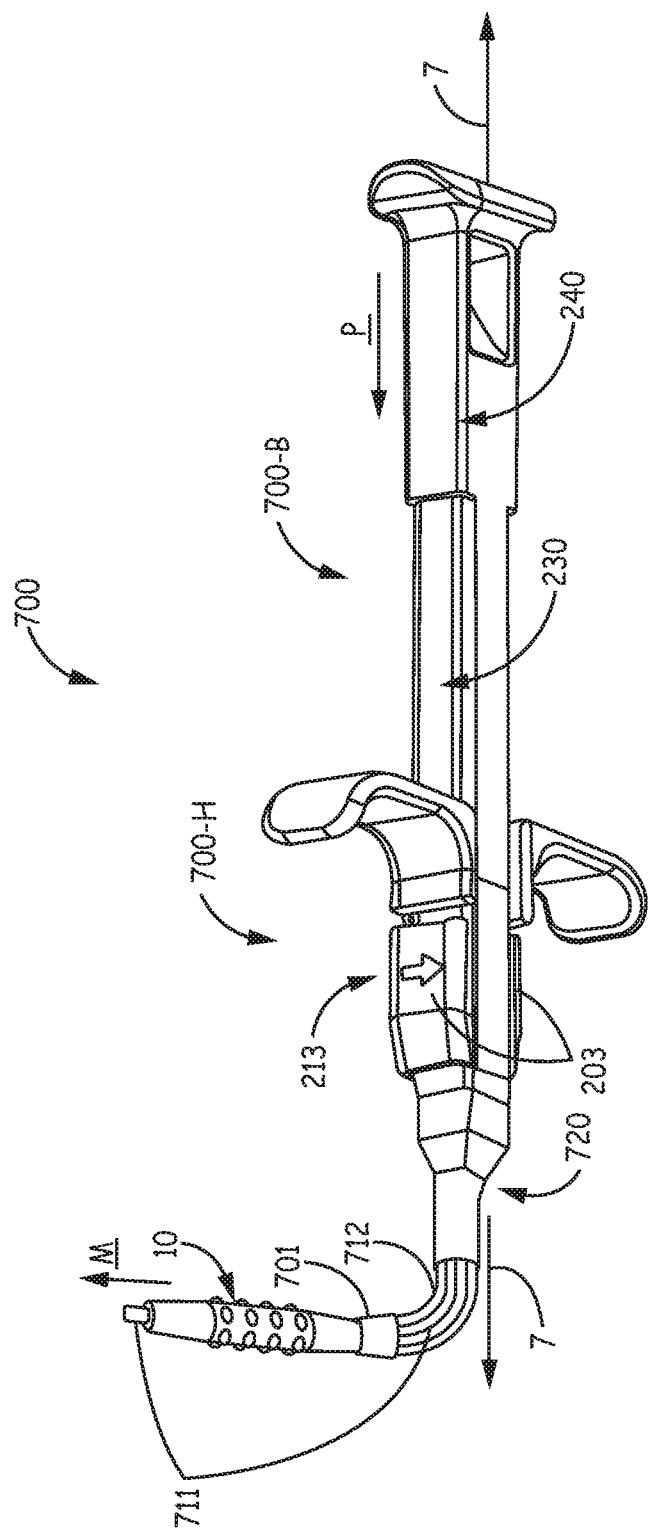
FIG. 7 is a perspective view, including a cut-away cross-section, of an exemplary deployment tool, according to yet further embodiments.

FIG. 7 is a perspective view of an exemplary deployment tool 700, according to yet further embodiments. FIG. 7 illustrates tool 700 including a base member 700-B and a handle member 700-H, which is held in sliding engagement with base member 700-B, and which includes an elongate tubular member 711 on which anchor sleeve 10B is mounted. Base member 700-B is similar to base member 200, described above, in that base member 700-B includes rail segment 230 and proximal segment 240; and handle member 700-H is similar to handle member 210, described above, in that handle member 700-H includes gripping segment 213 whose opposing arms 203 are fitted around rail segment 230 to hold handle member 700-H in sliding engagement with base member 700-B. Unlike handle member 210, a tubular member 711 of handle member 700-H includes a curved segment that extends between gripping segment 213 and a distal end portion of tubular member 711, to orient the distal end portion, about which anchor sleeve 10 is mounted, at an angle with respect to a longitudinal axis 7 of tool 700. Although not shown, it should be understood that tubular member 711 includes a lumen to receive a proximal length of an implanted elongate device, for example, like device 110 shown in FIG. 1A and in a manner similar to that shown in FIG. 1C.

FIG. 7 further illustrates a distal portion 720 of base member 700-B having a flexible wall 712, which is shown by a cut-away cross-section, to bend around the curved segment of tubular member 711, so that, when base member 700-B is pushed relative to handle 700-H, per arrow P, a deployment tip 701 of base member 700-B engages anchor sleeve 10 to move sleeve 10 off tubular member 711, per arrow M, and onto the implanted device. According to the illustrated embodiment, tool 700 is useful for deploying anchor sleeve 10 subcutaneously at an orientation approaching approximately parallel to a skin surface in which incision 12 (FIG. 1A) is made. Tubular member 711, like tubular member 211, preferably includes a lubricious coating that forms an outer surface thereof, to interface with the mounted anchor sleeve. Flexible wall 712 of base member distal segment 720 may be formed by a metal coil or braid embedded in a polymer material, according to methods known in the art.

Figure 8:
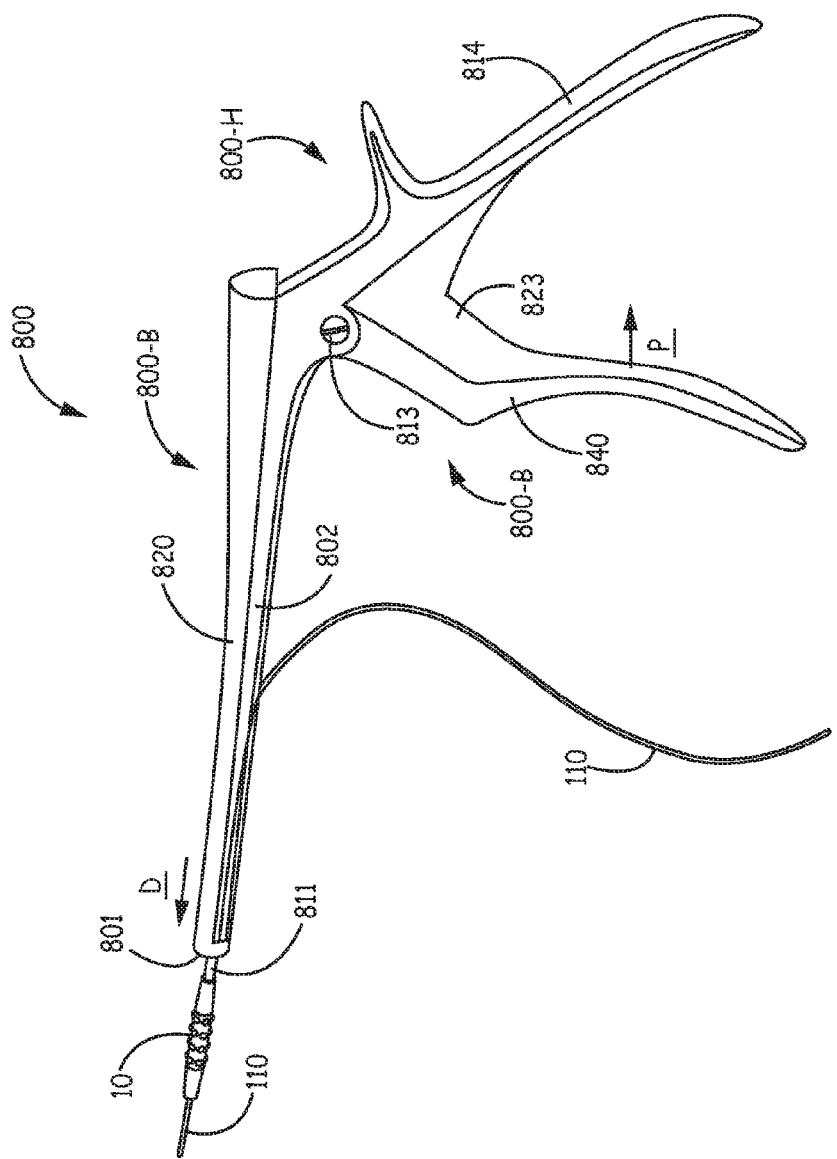
FIG. 8 is a perspective view of an exemplary deployment tool, according to another alternate embodiment.

FIG. 8 is a perspective view of an exemplary deployment tool 800, according to another alternate embodiment, wherein a base member 800-B and a handle member 800-H of tool 800 are slidably and pivotably engaged with one another. FIG. 8 illustrates base member 800-B including a longitudinal segment 820, which is sliding engagement around a longitudinal portion 802 of handle member 800-H, and which is terminated at a distal end thereof by a deployment tip 801. FIG. 8 further illustrates handle segment 800-H including a tubular member 811, which extends distally from longitudinal portion 802, and an abutment member 814, which extends proximally and laterally from longitudinal portion 802, and to which a trigger portion 840 of base member 800-B is pivotally coupled at a junction 813. According to the illustrated embodiment, and similar to the above-described embodiments, tubular member 811 of handle member 800-H has an outer surface sized for the mounting of anchor sleeve 10 thereon, as shown, and deployment tip 801 of base member 800-B is configured to engage with an end of the mounted anchor sleeve 10 and to move anchor sleeve 10 off from tubular member 811 and onto a proximal portion of device 110, which has been inserted through a lumen of tubular member 811 to extend out an opening in longitudinal portion 802 of handle member 800-H. With further reference to FIG. 8, longitudinal segment 820 of base member 800-B is pushed relative to handle portion 800-H, per arrow D, to deploy anchor sleeve 10, by pulling trigger portion 840 of base member 800-B, per arrow P, proximally toward abutment member 814 of handle member 800-H. Dashed lines in FIG. 8 depict that part of trigger portion 840 that joins with longitudinal segment 820 within a sidewall of handle portion 800-H. After deploying anchor sleeve 10, when trigger portion 840 is released, a bias of a spring member 823, which is shown coupled between trigger portion 840 and abutment member 814, returns base member 800-B to a 'pre-push' position with respect to handle member 800-H.

In the foregoing detailed description, specific exemplary embodiments have been described. However, it may be appreciated that various modifications and changes can be made without departing from the scope of the disclosure as set forth in the appended claims. Furthermore, deployment tools and kits for forming deployment tools, which include various combinations of features described above in conjunction with the specific embodiments, are within the scope of the present invention, for example, according to the following 13 statements that disclose features or combinations of features in exemplary embodiments:

1. In some exemplary embodiments, a tool for deploying an anchor sleeve onto an implantable elongate medical device, the tool comprising: a handle member including a gripping portion, an elongate tubular member extending distally from the gripping portion, and a junction between the tubular member and the gripping portion, the gripping portion defining a longitudinal axis of the tool, the tubular member having an outer surface sized for mounting the anchor sleeve thereon, and an inner surface defining a lumen extending longitudinally from a proximal opening, in proximity to the junction, to a distal opening, and the lumen being sized to receive a proximal length of the implantable device therein; and an elongate base member including a deployment tip and an elongate channel, the channel extending proximally from an opening at the deployment tip; wherein the channel of the base member receives the tubular member of the handle member in sliding engagement, when the gripping portion of the handle member is fitted around the base member; and the deployment tip of the base member is configured to engage with an end of the anchor sleeve, when the anchor sleeve is mounted on the tubular member of the handle member, and when the gripping portion of the handle member is fitted around the base member.

2. In some exemplary embodiments, the junction between the tubular member and the gripping portion of the handle member comprises: a bore hole, formed through an inner ridge of the gripping portion, the inner ridge extending between opposing arms of the gripping portion and being configured to fit in sliding engagement within the channel of the base member, when the opposing arms are fitted around the base member; a proximal length of the tubular member press fit within the bore hole; and a flared end of the tubular member, the flared end abutting a surface of the inner ridge of the gripping portion that extends around an opening of the bore hole.

3. Some exemplary embodiments include the tool of statement 1 or 2, wherein the outer surface of the tubular member of the handle member comprises a lubricious coating.

4. Some exemplary embodiments include the tool of any of statements 1-3, wherein the base member further includes holes formed through an exposed side of the base member, the exposed side extending between ends of opposing arms of the gripping portion of the handle member, when the arms are fitted around the base member.

5. Some exemplary embodiments include the tool of any of statements 1-4, wherein: the base member further comprises a rail segment and a proximal segment, the rail segment extending proximally from the deployment tip, and opposing arms of the gripping portion of the handle member extending around the rail segment, when the gripping portion is fitted around the base member; the channel of the base member extends through the rail segment and into the proximal segment; and the rail segment of the base member includes recessed sidewalls that extend distally from shoulders of the proximal segment, the shoulders of the proximal segment stopping the sliding engagement of the handle member along the rail segment.

6. Some exemplary embodiments include the tool of any of statements 1-5, wherein: the tubular member of the handle member includes a curved segment such that a distal end portion of the tubular member extends at an angle with respect to the longitudinal axis of the tool, when the opposing arms of the handle member are fitted around the base member; and the base member further comprises a distal segment, the distal segment being terminated by the deployment tip and being flexible to bend around the curved segment of the tubular member of the handle member, when the handle member is fitted around the base member.

7. Some exemplary embodiments include the tool of any of statements 1-4, wherein: the deployment tip of the base member is laterally offset from the longitudinal axis of the tool; an entirety of the tubular member of the handle member is laterally offset from the gripping portion of the handle member; and when the gripping portion of the handle member is fitted around base member, the tubular member of the handle member extends approximately parallel to the longitudinal axis of the tool.

8. Some exemplary embodiments include the tool of statement 7, wherein the lateral offsets of the tubular member of the handle member and of the deployment tip of the base member are adjustable.

9. Some exemplary embodiments include a tool kit for forming a tool according to any of statements 1-5, the tool kit comprising: a plurality of handle members, each handle member of the plurality according to any of statements 1-5; a plurality of anchor sleeves, each anchor sleeve of the plurality being mounted on the tubular member of a corresponding handle member of the plurality of handle members; and an elongate base member according to any of statements 1-5.

10. In some exemplary embodiments, the tool kit of statement 9, wherein the tool kit further forms a tool according to statement 8, the tool kit further comprising: another handle member according to statement 7; an anchor sleeve being mounted on the tubular member of the other handle member; and a converter configured for attachment to the distal segment of the base member, the converter including a leg member, an auxiliary distal segment, which extends from the leg member, and an auxiliary channel extending through the auxiliary distal segment, the auxiliary distal segment being laterally offset, by the leg member, from the rail segment of the base member, when the converter is attached to the distal segment of the base member; and wherein, when the converter is attached to the base member and the other handle member is held in sliding engagement with the base member, the auxiliary channel of the auxiliary distal segment of the converter is located to receive the tubular member of the other handle member.

11. In some exemplary embodiments, the tool kit of statement 10, wherein the lateral offsets of the tubular member of the other handle member and the auxiliary distal segment of the converter are adjustable.

12. In some exemplary embodiments, the tool kit of statement 10, wherein: the lateral offset of the tubular member of the other handle member is adjustable; and the converter is one of a plurality of converters included in the kit, each converter having a different lateral offset of the corresponding auxiliary distal segment, to accommodate the adjustable lateral offset of the tubular member of the other handle member.

13. Some exemplary embodiments include the tool kit of any of statements 9-12, wherein the base member further comprises a marked portion to guide alignment of the gripping portion of any one of the plurality of handle members when fitting opposing arms of the gripping portion around the base member.

The invention claimed is:

1. A method for deploying an anchor sleeve onto a body of an implantable elongate medical device, the method comprising the steps of:
    selecting and removing one of a plurality of handle members from an anchoring tool kit, each of the plurality of handle members carrying an anchor sleeve, each anchor sleeve being mounted around a distal end portion of an elongate tubular member of the corresponding handle member, and each elongate tubular member extending from a gripping portion of the corresponding handle member;
    inserting a proximal length of the implantable device through a lumen of the tubular member of the selected handle member of the plurality of handle members;
    removing an elongate base member from the anchoring tool kit and aligning a marked portion of a rail segment of the base member with the gripping portion of the selected handle member, the marked portion extending over a length of the rail segment in proximity to a distal segment of the base member;
    engaging the marked portion of the base member with the gripping portion of the selected handle member such that a segment of the tubular member of the selected handle member is received within a channel of the base member, the segment extending between the corresponding gripping portion and the mounted anchor sleeve of the selected handle member;
    pushing the engaged base member, relative to the selected handle member to move the anchor sleeve off from the tubular member and onto the inserted proximal length of the implantable device.

2. The method of claim 1, wherein the distal end portion of the elongate tubular member of the selected handle member is laterally offset from the gripping portion thereof, and further comprising:
    selecting and removing a converter from the anchoring tool kit; and
    coupling the converter member to the distal segment of the base member, the converter member including the channel of the base member that receives the segment of the tubular member, the channel being laterally offset, by a leg member of the converter, from the rail segment of the base member, when the converter is coupled to the base member.

3. The method of claim 2, further comprising adjusting the lateral offset of the channel of the converter.

4. The method of claim 1, wherein engaging the marked portion of the base member with the gripping portion of the selected handle member comprises inserting the marked portion between opposing arms of the gripping portion.

5. The method of claim 1, wherein the step of pushing the engaged base member comprises engaging a finger of a hand with a laterally extending tab element of the handle member while abutting another portion of the hand against a proximal surface of the engaged base member, the proximal surface of the base member being located proximal to the marked portion thereof.

6. The method of claim 1, wherein the step of inserting the proximal length of the implantable device precedes the step of engaging the marked portion of the base member.

7. The method of claim 1, further comprising monitoring a movement of the marked portion of the engaged base member relative to the gripping portion of the handle member, while pushing the engaged base member.

* * * * *